United States Patent [19]

Mauldin

[11] Patent Number: 4,513,161
[45] Date of Patent: Apr. 23, 1985

[54] CONVERSION OF METHANOL TO HYDROCARBONS

[75] Inventor: Charles H. Mauldin, Baton Rouge, La.

[73] Assignee: Exxon Research and Engineering Co., Florham Park, N.J.

[21] Appl. No.: 626,025

[22] Filed: Jun. 29, 1984

[51] Int. Cl.$^3$ .............................................. C07C 1/00
[52] U.S. Cl. .................................... 585/640; 585/733; 502/325
[58] Field of Search .................. 585/640, 733; 502/325

[56] References Cited

U.S. PATENT DOCUMENTS

| | | | |
|---|---|---|---|
| 4,088,671 | 5/1978 | Kobylinski | 260/449 |
| 4,338,089 | 7/1982 | Schaper et al. | 518/707 |
| 4,385,193 | 5/1983 | Bijwaard et al. | 585/310 |

FOREIGN PATENT DOCUMENTS 2073237  3/1981  United Kingdom ................ 332/385

OTHER PUBLICATIONS

92:129385h; The Synthesis of Solid Hydrocarbons From Methanol; Shima, Kensuke, Morita, Tauyoshi, (Miyazaki Univ., Miyazaki, Japan); Nouveau Journal DeChime, vol. 6, No. 10—1982, p. 459.
Fischer–Tropsch Synthesis of Hydrocarbons Over Ruthenium Supported on Transition Metal Oxides; Kikuchi, Nomura, Matsumoto and Morita, (Waseda University, Tokyo 160); Pan–Pacific Synfuels Conference, vol. I, Nov. 17-19, 1982 Tokyo, pp. 1-10.
Fischer–Tropsch Synthesis Over Titania–Supported Ruthenium Catalysts; Kikuchi, Matsumoto, Takahashi, Machino and Morita, (Waseda University, 3-4-1 Okubo, Shinjuku, Tokyo, Japan); Printed in The Netherlands; Applied Catalysis, 10 (1984), pp. 251-260.
IS-T-1006; Hydrogenation of Carbon Monoxide Over Ruthenium–rhenium on Alumina Catalysts; D. E. Whitmoyer (M.S. Thesis submitted to Iowa State University); Prepared for the U.S. Department of Energy Under Contract No. W-7405-eng-82; Jul. 1982.

*Primary Examiner*—Delbert E. Gantz
*Assistant Examiner*—Cynthia A. Prezlock
*Attorney, Agent, or Firm*—Llewellyn A. Proctor

[57] ABSTRACT

A process wherein methanol is contacted, in the presence of hydrogen, over a ruthenium-titania catalyst to produce, at reaction conditions, an admixture of $C_{10}+$ linear paraffin and olefins, which can be further refined and upgraded to high quality middle distillate fuels, and other valuable products such as mogas, diesel fuel, jet fuel, lubes, and specialty solvents, especially premium middle distillate fuels of carbon number ranging from about $C_{10}$ to $C_{20}$.

9 Claims, No Drawings ized, useful in combination with an upstream conventional methanol synthesis plant.

CONVERSION OF METHANOL TO HYDROCARBONS

BACKGROUND AND PROBLEMS

I. Field of the Invention

This invention relates to a process for the preparation of liquid hydrocarbons from methanol. In particular, it relates to a process wherein $C_{10}+$ distillate fuels and other valuable products are prepared by reaction of methanol, and hydrogen, over a ruthenium catalyst.

II. The Prior Art

Methane is often available in large quantities from process streams either as an undesirable by-product in admixture with other gases, or as an off gas component of a process unit, or units. More importantly, however, methane is the principle component of natural gas, and it is produced in considerable quantities in oil and gas fields. The existence of large methane, natural gas reserves coupled with the need to produce premium grade transportation fuels, particularly middle distillate fuels, creates a large incentive for the development of a new gas-to-liquids process. Conventional technology, however, is not entirely adequate for such purpose. Nonetheless, technology is available for conversion of synthesis gas, which can be obtained from coal or natural gas, to produce methanol, a product of currently limited marketability. However, to utilize the existing technology, there is a need for a process suitable for the conversion of methanol to high quality transportation fuels, particularly middle distillate fuels.

III. Objects

It is, accordingly, a primary objective of the present invention to supply this need.

A particular object is to provide a novel process useful for the conversion of methanol to admixtures of $C_{10}+$ linear paraffins and olefins which can be further refined and upgraded to high quality middle distillate fuels, and other valuable products.

A particular object is to provide a process as characterized, useful in combination with an upstream conventional methanol synthesis plant.

IV. The Invention

These objects and others are achieved in accordance with the present invention embodying a process wherein methanol is contacted, in the presence of hydrogen, over a ruthenium-titania catalyst to produce, at reaction conditions, an admixture $C_{10}+$ linear paraffin and olefins, which can be further refined and upgraded to high quality middle distillate fuels, and other valuable products such as mogas, diesel fuel, jet fuel, lubes, and specialty solvents, especially premium middle distillate fuels of carbon number ranging from about $C_{10}$ to $C_{20}$.

The ruthenium-titania catalyst is one wherein ruthenium is composited, or dispersed upon titania ($TiO_2$), or a titania-containing carrier, or support. The ruthenium is dispersed on the support in catalytically effective amounts. Suitably, in terms of absolute concentration, the ruthenium is dispersed on the support in amounts ranging from about 0.01 percent to about 8 percent, preferably from about 0.2 percent to about 4 percent, based on the total weight of the catalyst composition. These catalyst compositions, it has been found, produce at reaction conditions a product which is predominantly $C_{10}+$ linear paraffins and olefins, with very little oxygenates. These catalysts provide high selectivity, high activity and good activity maintenance in the conversion of methanol to $C_{10}+$ hydrocarbons.

In conducting the reaction the total pressure must be maintained above about 160 pounds per square inch gauge (psig), and preferably above about 225 psig, and it is generally desirable to employ methanol, and hydrogen, in molar ratio of $CH_3OH:H_2$ of at least about 2:1 and preferably at least about 4:1 to increase the concentration of $C_{10}+$ hydrocarbons in the product. Suitably, the $CH_3OH:H_2$ molar ratio ranges from about 2:1 to about 50:1, and preferably the methanol and hydrogen are employed in molar ratio ranging from about 4:1 to about 40:1. In general, the reaction is carried out at liquid hourly space velocities ranging from about 0.1 $hr^{-1}$ to about 10 $hr^{-1}$, preferably from about 0.2 $hr^{-1}$ to about 2 $hr^{-1}$, and at temperatures ranging from about 150° C. to about 350° C., preferably from about 180° C. to about 250° C. Pressures range from about 160 psig to about 800 psig, preferably from about 225 psig to about 500 psig. The product generally and preferably contains 50 percent, or greater, $C_{10}+$ liquid hydrocarbons which boil above about 160° C. (320° F.).

Ruthenium/titania catalysts exhibit high activity and selectivity in the conversion of a feed consisting essentially of methanol, and hydrogen, to $C_{10}+$ middle distillates. The catalysts employed in the practice of this invention may be prepared by techniques known in the art for the preparation of these and other catalysts. The catalyst can, e.g., be prepared by gellation, or cogellation techniques. Suitably, however, ruthenium can be composited alone, or with another metal, or metals, upon a previously pilled, pelleted, beaded, extruded, or sieved titania or titania-containing support material by the impregnation method. Suitably the ruthenium is composited with the support by contacting the support with a solution of a ruthenium-containing compound, or salt, e.g., a nitrate, chloride or the like. The amount of impregnation solution used should be sufficient to completely immerse the carrier, usually within the range from about 1 to 20 times the carrier by volume, depending on the concentration of the ruthenium-containing compound in the impregnation solution. The impregnation treatment can be carried out under a wide range of conditions including ambient or elevated temperatures. Metal components other than ruthenium may also be added as promoters. The introduction of another metal, or metals, into the catalyst can be carried out by any method and at any time of the catalyst preparation, for example, prior to, following or simultaneously with the impregnation of the support with the ruthenium component. In the usual operation, the additional component is introduced simultaneously with the incorporation of the ruthenium component.

The catalyst, after impregnation, is dried by heating at a temperature above about 25° C., preferably between about 65° C., and 150° C., in the presence of nitrogen or oxygen, or both, in an air stream or under vacuum. The metal, or metals, contained on the catalyst can then be reduced. Reduction is performed by contact of the catalyst with hydrogen or a hydrogen-containing gas stream at temperatures ranging from about 180° C. to about 575° C. for periods ranging from about 0.5 to about 24 hours at pressures ranging from ambient to about 40 atmospheres. A gas containing hydrogen and inert components, or a gas containing hydrogen and carbon monoxide in admixture are satisfactory for use in carrying out the reduction.

The invention will be more fully understood by reference to the following demonstrations and examples which present comparative data illustrating its more salient features.

The data given in the examples which follow were obtained in a small fixed bed reactor unit, conventional material balance work-up having been obtained during the runs which were conducted over 24 to 100 hour periods. All parts are in terms of weight units except as otherwise specified.

The "Schulz-Flory Alpha" is a known method for describing the product distribution in Fischer-Tropsch synthesis reactions, and it is also useful in describing the product distribution from methanol conversion reactions. The Schulz-Flory Alpha is the ratio of the rate of chain propagation to the rate of propagation plus termination, and is described from the plot of 1n (Wn/n) versus n, where Wn is the weight fraction of product with a carbon number of n. In the examples below, an Alpha value was derived from the $C_{10}/C_{20}$ portion of the product. The Alpha value is indicative of the selectivity of the catalyst for producing heavy hydrocarbons from the methanol, and is indicative of the amount of $C_{10}+$ hydrocarbons in the product. For example, a Schulz-Flory Alpha of 0.80 corresponds to about 35% by weight of $C_{10}+$ hydrocarbons in the product, a generally acceptable level of $C_{10}+$ hydrocarbons. A Schulz-Flory Alpha of 0.85, a preferred Alpha value, corresponds to about 54% by weight of $C_{10}+$ hydrocarbons in the products, and a Schulz-Flory Alpha of 0.90, a more preferred Alpha value, corresponds to about 74% by weight of $C_{10}+$ hydrocarbons in the product.

The ruthenium-titania catalysts used in the examples below were prepared by the following procedure:

Titania (Degussa P-25 $TiO_2$) was used as the support after mixing with sterotex, and after pilling, grinding, and screening to 80–150 mesh (Tyler). The titania was calcined in air and reduced with $H_2$ at 500° C. to provide a support containing a rutile:anatase ratio of 2:1 (ASTM D 3720-78: Standard Test Method for Ratio of Anatase to Rutile in Titanium Dioxide Pigments by Use of X-Ray Diffraction) with a surface area of 23 m²/g and a pore volume of 0.24 ml/gm. Catalysts, of 80–150 mesh size, were prepared by simple impregnation of the support with ruthenium nitrate (Engelhard) from acetone solution using a rotary evaporator, drying in a vacuum oven at 150° C. These catalysts were charged to a reactor, reduced in $H_2$ at 450° C. for one hour, and then reacted with methanol at the conditions described in the examples.

In the example which immediately follows a ruthenium-titania catalyst is compared with a known German cobalt catalyst, and with a fused iron catalyst.

EXAMPLE 1

A feed constituted of an admixture of methanol and hydrogen in $CH_3OH:H_2$ molar ratio of 4:1 was contacted (1), in a first run, with a ruthenium-titania catalyst (1% Ru-$TiO_2$), in a second run with a cobalt-thoria catalyst on kieselguhr (100 Co-5 $ThO_2$-8 MgO-200 kieselguhr), and (3) in a third run with a carbided fused iron catalyst (Fused Fe, carbided by treatment with 1:1 $H_2/CO$ at 230° C.) at 230° C., 280 psig, and GHSV=500. Reference is made to Table I.

TABLE I

| 230° C., 280 psig, $CH_3OH/H_2$ = 4, GHSV = 500 | | | |
|---|---|---|---|
| | Ru—$TiO_2$ | 100 Co—5 $ThO_2$—8 MgO—200 Kieselguhr[1] | Fused Fe[2] Carbided |
| $CH_3OH$ Conversion at 10 Hr., Wt % | 93 | 98 | 28 |
| Carbon Product Distribution, Wt % | | | |
| CO | 0.6 | 1.7 | 2.8 |
| $CO_2$ | 15.6 | 36.6 | 48.7 |
| $CH_4$ | 26.5 | 31.4 | 5.5 |
| $C_2+$ | 57.3 | 30.3 | 43.0 |
| Hydrocarbon Space Time Yields, G/HR/CC | 0.21 | 0.19 | 0.05 |

[1]Prepared by Procedure given at Page 137 and following: The Fischer-Tropsch and Related Syntheses, Storch, Golumbic and Anderson, John Wiley and Sons, Inc., New York (1951).
[2]Katalco 35-4

Ru-$TiO_2$, it will be observed, provides the best activity and selectivity to $C_2+$ hydrocarbons compared to the cobalt catalyst, or to the fuel iron carbided catalyst. The poor performance of fused iron is particularly interesting in view of its long commercial use and recognized high activity in conducting Fischer-Tropsch synthesis reactions to produce hydrocarbons from syn gas. The cobalt catalyst shows surprisingly high activity, good space time yields, and the ability to produce hydrocarbons. However, the cobalt catalyst as shown in the following Example 2 (Table II), produces high $CO_2$, a debit when contrasted with Ru-$TiO_2$.

EXAMPLE 2

Example 1 was repeated utilizing the Ru-$TiO_2$ and cobalt-thoria catalysts, except that the reaction utilizing the cobalt-thoria catalyst was conducted at 200° C., and in conducting both reactions the feed gas was diluted with argon to maintain good operability in terms of obtaining acceptable material balances. Reference is made to Table II.

TABLE II

| 280 psig, $CH_3OH/H_2/Ar$ = 20/1/4, GHSV = 500 | | |
|---|---|---|
| | Ru—$TiO_2$ | Co—$ThO_2$—MgO—Kieselguhr |
| Temperature, °C. | 230 | 200 |
| $CH_3OH$ Conversion at 35 hr., Wt. % | 26 | 33 |
| Carbon Product Distribution, Wt. % | | |
| CO | 11 | 3 |
| $CO_2$ | 9 | 43 |
| $CH_4$ | 12 | 9 |
| $C_2+$ | 68 | 45 |
| Schulz-Flory Alpha | 0.82 | 0.83 |

The Schulz-Flory Alpha values for both catalysts, it will be observed, are quite high indicating a conversion of methanol to $C_{10}+$ hydrocarbons approximating 50 percent. The lower rate of conversion of the feed to $CO_2$ for the Ru-$TiO_2$ catalyst, however, renders this the superior catalyst. The ruthenium catalyst thus behaves more ideally than the cobalt catalyst in that more of the methanol is converted to hydrocarbons and water in accordance with the equation: $xCH_3OH \rightarrow (CH_2)_x + xH_2O$; with less conversion to carbon dioxide.

EXAMPLE 3

The liquid hydrocarbon product made from Ru-$TiO_2$ consists primarily of linear olefins and paraffins. The product contains more isomers than a product made by a Fischer-Tropsch reaction utilizing a Ru-TiO$_2$ catalyst. Reference is made to Table III which shows the distribution of compounds within the C$_8$ fraction of the product obtained by reaction of the methanol, and hydrogen over the Ru-TiO$_2$ catalyst at the conditions described in Example 1 vis-a-vis a typical Fischer-Tropsch product produced by conversion of CO and H$_2$ over Ru-TiO$_2$ at comparable conditions.

TABLE III

| C$_8$ Distribution | 230° C., 280 psig | |
|---|---|---|
| | CH$_3$OH | CO |
| n-Paraffin | 67.4 | 62.1 |
| Iso-Paraffins | 6.5 | 0.7 |
| α-Olefin | 1.4 | 23.5 |
| Internal Olefins | 21.6 | 13.1 |
| Iso-Olefins | 3.1 | 0.3 |
| Alcohol | 0.0 | 0.3 |

As suggested, the product is more isomerized than the product from a Fischer-Tropsch syn gas using a Ru-TiO$_2$ catalyst. Isomerization of the double bond from terminal to internal positions of the linear olefins and greater production of branched paraffins and olefins occur with methanol. The small amount of oxygenates formed from the Fischer-Tropsch synthesis reaction are absent in the product of the methanol reaction.

Hydrogen, in relatively small amount is required to promote conversion of the methanol to hydrocarbons. The absolute hydrogen concentration is also of importance in promoting conversion, selectivity and yield in the production of the C$_{10}+$ hydrocarbons from methanol. Partial pressures less than about 20 psia, preferably less than 10 psia produce the higher molecular weight liquid hydrocarbons. H$_2$ partial pressure above about 20 psia, or even 10 psia favors a lighter, more paraffinic product. This is demonstrated in the example immediately following.

EXAMPLE 4

An admixture constituted of methanol and argon to which hydrogen was added in varying concentrations was passed into a reactor charged with a Ru-TiO$_2$ catalyst, at 230° C., CH$_3$OH=236 psia, argon (59-H$_2$ psia) and GHSV=500. Measurements were made after 35 hours and 60 hours, respectively, of the CH$_3$OH conversion, and carbon product distribution in terms of weight percent hydrocarbons, carbon monoxide, and carbon dioxide formation. Measurements were also made of the weight percent methane in the hydrocarbon product and the Schulz-Flory Alpha. The results are given in Table IV.

TABLE IV

| 230° C., CH$_3$OH = 236 psia, Inert = (59-H$_2$ psia), GHSV = 500 | | | |
|---|---|---|---|
| Inlet H$_2$ Partial Pressure, psia | 0 | 12 | 59 |
| CH$_3$OH Conversion | 13 | 32 | 76 |
| Carbon Product Distribution; Wt % | | | |
| CO | 38 | 7 | 1 |
| CO$_2$ | 4 | 8 | 12 |
| CH$_4$ | 3 | 11 | 24 |
| C$_2$+ | 55 | 74 | 63 |
| Wt. % CH$_4$ in Hydrocarbon | 6 | 13 | 28 |
| Schulz-Flory Alpha | 0.93 | 0.83 | 0.73 |

These data show that at "0" psig conversion of the methanol is very low, i.e., about 13%, and the selectivity to hydrocarbons is also relatively low, i.e., about 58%. At about 12 psia hydrogen partial pressure the rate of conversion is essentially doubled, and the amount of hydrocarbons produced rises to about 85%. The CO make is decreased quite drastically and the CO$_2$ make remains at an acceptably low level. The make of light hydrocarbon gas is relatively low, and the Schulz-Flory Alpha value remains above 0.8. The high H$_2$ partial pressure, i.e., 59 psia, provides excellent conversion but leads to a lighter hydrocarbon product as indicated by the higher methane and lower Schulz-Flory Alpha.

The following data demonstrates that the total pressure at which the reaction is conducted promotes hydrocarbon conversion.

EXAMPLE 5

A series of runs were made wherein argon, methanol and hydrogen were injected into the reactor, the CH$_3$OH:H$_2$ ratio being held constant, while the total pressure was gradually increased between ambient pressure, or "0" psig and 400 psig. These runs were conducted, while the argon, methanol and hydrogen were injected at a constant rate of flow, at 230° C. and GHSV=500. Reference is made to Table V.

TABLE V

| 230° C., GHSV-500, CH$_3$OH/H$_2$/Ar = 20/1/4 | | | | |
|---|---|---|---|---|
| Pressure, psig | 0 | 60 | 280 | 400 |
| CH$_3$OH Conversion | 18 | 18 | 32 | 36 |
| Carbon Product Distribution, Wt % | | | | |
| CO | 95 | 81 | 7 | 5 |
| CO$_2$ | 1 | 3 | 8 | 12 |
| CH$_4$ | 1 | 5 | 11 | 10 |
| C$_2$+ | 3 | 11 | 74 | 73 |

These data show that, at the stated conditions, over about 160 psig of total pressure of CH$_3$OH and H$_2$ is desired at reasonable space velocities to ensure conversion of the methanol to hydrocarbons; rather than producing a conversion of the methanol to significant amounts of carbon monoxide (CO) and hydrogen. Lower pressures can also produce hydrocarbons, but an undesirable lowering of the space velocity may be required. Longer residence time, in contrast, leads to conversion of the CO intermediate to hydrocarbons via normal Fischer-Tropsch chemistry. However, such an option fails to provide the credits and advantages offered by the methanol conversion process of this invention. Thus, the build-up of CO can and should be avoided and this can be done without sacrificing through-put by the use of pressure over about 160 psig, preferably over about 225 psig, of CH$_3$OH/H$_2$.

EXAMPLE 6

The procedure of Example 1 was repeated, data being obtained at 35 hours. One run was made without CO addition (Column 1) and in another run (Column 2) CO was added to the methanol feed.

The build-up of CO in the reaction mixture, or product should be avoided, supra. Evidence of this is provided by the following example in which CO was added to a methanol run. As shown in Table VI, added CO dramatically poisons the methanol conversion reaction. This surprising result can be rationalized on the theory that there exists a strong competitive adsorption effect, i.e., the strong adsorption of CO on the catalyst, which simply prevents appreciable adsorption of methanol on the active sites of the catalyst.

TABLE VI

|  | $CH_3OH$ | $CH_3OH + CO$ |
|---|---|---|
| Temperature, °C. | 230 | 230 |
| GHSV 500 | 500 | 560 |
| Inlet psia. | | |
| $CH_3OH$ | 236 | 236 |
| $H_2$ | 59 | 59 |
| CO | 0 | 31 |
| Inert | 0 | 4 |
| Conversions at 35 Hr. | | |
| $CH_3OH$ | 76 | <3 |
| CO | — | 84 |

The present process is highly suitable for the conversion of methanol to hydrocarbons over ruthenium catalysts. The reaction can be conducted in fixed bed, slurry, or fluidized bed reactors with or without the recycle of any unconverted methanol, gas and/or liquid product. Total pressure is maintained over about 160 psig, preferably over about 225 psig. The mole ratio of methanol to $H_2$ should be above about 2:1, and preferably above about 4:1 if a high portion of $C_{10}+$ hydrocarbons are desired. The $C_{10}+$ product admixture of linear paraffins and olefins can be further refined and upgraded to high quality middle distillate fuels, or such other products as mogas, diesel fuel, jet fuel, lubes, specialty solvents and the like. A premium grade middle distillate fuel of carbon number ranging from about $C_{10}$ to about $C_{20}$ can also be produced from the $C_{10}+$ hydrocarbon product. The catalyst is constituted of ruthenium supported on $TiO_2$ or titania-containing support containing such non-acidic materials as $SiO_2$, $MgO$, $ZnO_2$, and $Al_2O_3$. The catalyst is preferably reduced with a $H_2$-containing gas at start-up.

It is apparent that various modifications and changes can be made without departing the spirit and scope of the present invention.

What is claimed is:

1. A process useful for the conversion of methanol to hydrocarbons which comprises contacting at reaction conditions a feed comprised of an admixture of methanol and hydrogen, in methanol:hydrogen molar ratio equal to or greater than about 2:1 at total pressure equal to or greater than about 160 psig, over a catalyst which comprises ruthenium in catalytically active amount composited with titania or titania-containing support.

2. The process of claim 1 wherein the catalyst contains from about 0.01 percent to about 8 percent ruthenium, based on the weight of the catalyst composition.

3. The process of claim 1 wherein the catalyst contains from about 0.2 to about 4 percent ruthenium, based on the weight of the catalyst composition.

4. The process of claim 1 wherein the molar ratio of methanol:hydrogen ranges from about 2:1 to about 50:1.

5. The process of claim 4 wherein the molar ratio of methanol:hydrogen ranges from about 4:1 to about 40:1.

6. The process of claim 1 wherein the total pressure of the reaction ranges above about 225 psig.

7. The process of claim 6 wherein the total pressure of the reaction ranges from about 225 psig to about 500 psig.

8. The process of claim 1 wherein the reaction conditions are defined within ranges as follows:
Methanol:$H_2$ ratio about 2:1 to 50:1
Liquid Hourly Space Velocities, $hr^{-1}$ about 0.1 to 10
Temperatures, °C. about 150 to 350
Total Pressure, psig 160 to 800.

9. The process of claim 8 wherein the reaction conditions are defined within ranges as follows:
Methanol:$H_2$ mole ratio about 4:1 to 40:1
Liquid Hourly Space Velocities, $hr^{-1}$ about 0.2 to 2
Temperatures, °C. about 180 to 250
Total Pressure, psig about 225 to 500.

* * * * *